(12) United States Patent
Mosca

(10) Patent No.: US 7,579,007 B2
(45) Date of Patent: *Aug. 25, 2009

(54) PRODUCTION OF "BIOLOGICAL CARRIERS" FOR INDUCTION OF IMMUNE RESPONSES AND INHIBITION OF VIRAL REPLICATION

(75) Inventor: Joseph D. Mosca, Ellicott City, MD (US)

(73) Assignee: JDM Technologies, Inc., Ellicott City, MD (US)

( * ) Notice: Subject to any disclaimer, the term of this patent is extended or adjusted under 35 U.S.C. 154(b) by 176 days.

This patent is subject to a terminal disclaimer.

(21) Appl. No.: 10/468,047

(22) PCT Filed: Feb. 12, 2002

(86) PCT No.: PCT/US02/04157

§ 371 (c)(1),
(2), (4) Date: Aug. 13, 2003

(87) PCT Pub. No.: WO02/079396

PCT Pub. Date: Oct. 10, 2002

(65) Prior Publication Data

US 2004/0116367 A1    Jun. 17, 2004

Related U.S. Application Data

(60) Provisional application No. 60/268,066, filed on Feb. 13, 2001.

(51) Int. Cl.
*A61K 39/00* (2006.01)
*A61K 39/12* (2006.01)
*A61K 39/21* (2006.01)
*C12N 7/04* (2006.01)
*C12P 21/00* (2006.01)
*C12N 15/09* (2006.01)

(52) U.S. Cl. ............... 424/204.1; 435/69.1; 435/69.3; 435/235.1; 435/236; 435/239; 424/184.1; 424/208.1

(58) Field of Classification Search ............ 435/235.1, 435/236, 325, 69.1, 69.3, 70.1, 70.3; 424/184.1, 424/199.1, 204.1, 208.1, 278.1, 93.1, 93.2, 424/93.6; 536/23.7, 23.72

See application file for complete search history.

(56) References Cited

U.S. PATENT DOCUMENTS 5,306,631 A * 4/1994 Harrison et al. ............ 435/461
5,855,891 A * 1/1999 Lowy et al. ............... 424/192.1
6,149,906 A * 11/2000 Mosca ...................... 424/93.7

FOREIGN PATENT DOCUMENTS

WO    WO 99/15199    *    4/1999

OTHER PUBLICATIONS

Cantin et al., "The Amount of Host HLA-DR Proteins Acquired by HIV-1 Is Virus Strain- and Cell Type-Specific," Virology, vol. 218 No. 2, pp. 372-381 (Apr. 1996).*
Esser et al., "Differential Incorporation of CD45, CD80 (B7-1), CD86 (B7-2), and Major Histocompatibility Complex Class I and II Molecules into Human Immunodeficiency Virus Type 1 Virions and Microvesicles: Implications for Viral Pathogenesis and Immune Regulation," Journal of Virology, vol. 75 No. 13, pp. 6173-6182 (Jul. 2001).*
Oertli et al., "Artificial antigen-presenting cells engineered by recombinant vaccinia viruses expressing antigen, MHC class II, and costimulatory molecules elicit proliferation of CD4+ lymphocytes in vitro ," Clincal and Experimental Immunology, vol. 110 No. 1, pp. 144-149 (Sep. 1997).*
Roy et al., "HIV type 1 can act as an APC upon acquisition from the host cell of peptide-loaded HLA-DR and CD86 molecules," Journal of Immunology, vol. 174 No. 8, pp. 4779-4788 (Apr. 2005).*
Rossio et al., "HLA class II on HIV particles is functional in superantigen presentation to human T cells: implications for HIV pathogenesis", AIDS Research and Human Retroviruses, vol. 11 No. 12, pp. 1433-1439 (Dec. 1995).*
Tremblay et al., "The acquisition of host-encoded proteins by nascent HIV-I," Immunology Today, vol. 19, pp. 345-350 (1998).*
Giguère et al., "Insertion of Host-Derived Costimulatory Molecules CD80 (B7.1) and CD86 (B7.2) into Human Immunodeficiency Virus Type 1 Affects the Virus Life Cycle," Journal of Virology, vol. 78 No. 12, pp. 6222-6232 (Jun. 2004).*
Chang, Efficient amplification of melanoma-specific CD8+ T cells using artificial antigen presenting complex, Experimental and Molecular Medicine, vol. 38 No. 6, pp. 591-598 (2006).*
Derdak et al., "Direct stimulation of T lymphocytes by immunosomes: Virus-like particles decorated with T cell receptor/CD3 ligands plus costimulatory molecules," Proceedings of the National Academy of Sciences, USA, vol. 103 No. 35, pp. 13144-13149 (2006).*
Kim et al., "The ABCs of artificial antigen presentation," Nature Biotechnology, vol. 22, pp. 403-410 (2004).*
Moody et al., "Anatomy of CD1-Lipid antigen complexes," Nature Reviews, Immunology, vol. 5 No. 5, pp. 387-399 (May 2005).*
Zajonc et al., "CD1 mediated T cell recognition of glycolipids," Current Opinion in Structural Biology, vol. 17, Issue 5, Oct. 2007, pp. 521-529.*

* cited by examiner

*Primary Examiner*—Zachariah Lucas
(74) *Attorney, Agent, or Firm*—Patentique PLLC

(57) ABSTRACT

This application provides a method to form non-infectious Biological Carrier that may be used to deliver signals to cells either in vitro or in vivo. The Biological Carriers are inactivated virus particles that have been specifically modified to give biological properties different from the virus particles deriving from an unmodified host cell that (i) expresses at least one co-stimulatory molecule and (iia) at least one antigen that can initiate an immune response, and/or (iib) express surface molecules that suppress viral replication.

16 Claims, 11 Drawing Sheets

Schematic Representation of the Interaction of Biological Carrier Preparations with Dominant T-lymphocyte Populations

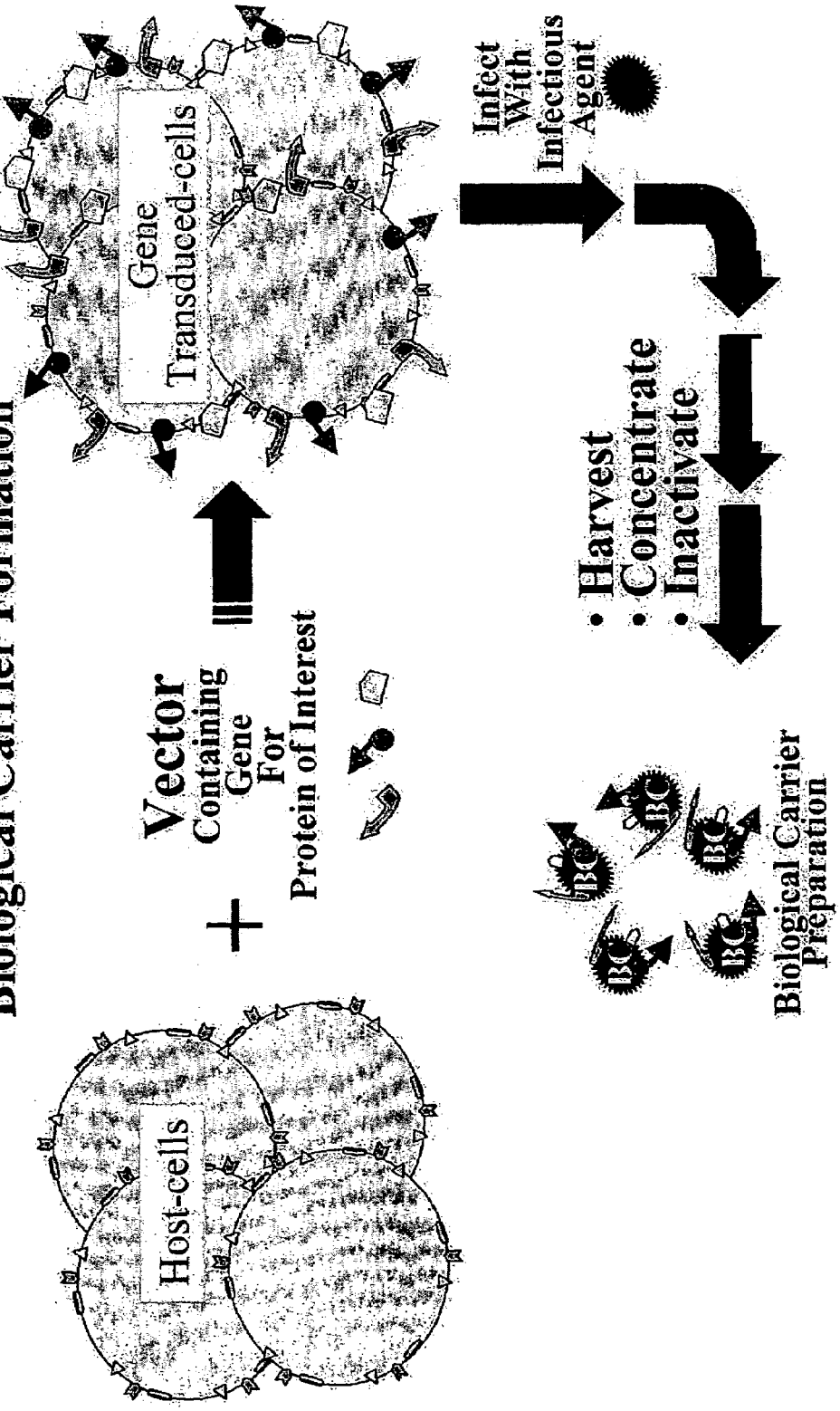

Figure 2

Lack of T-lymphocyte Stimulation by either HSV-2 or HIV-1 based Biological Carrier Preparations Prepared from Untransduced Cells Elutriated T-lymphocytes +/- HIV-1 Infection Elutriated T-lymphocytes Exposed to
HIV-1 based Biological Carriers

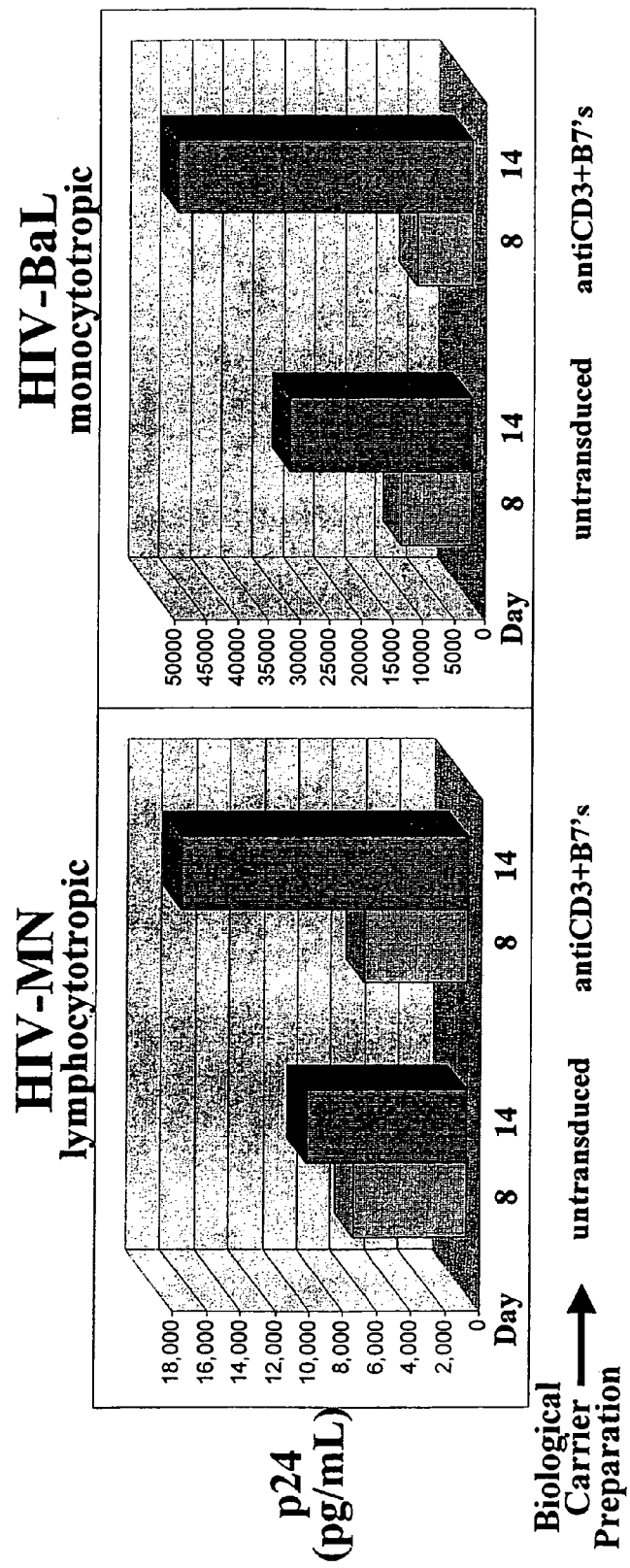

PRODUCTION OF "BIOLOGICAL CARRIERS" FOR INDUCTION OF IMMUNE RESPONSES AND INHIBITION OF VIRAL REPLICATION

PRIORITY DOCUMENTS

This application is a 371 application of PCT/US02/04157, filed Feb. 12, 2002, which claims priority to U.S. Provisional application 60/268,066, filed Feb. 13, 2001.

FIELD OF THE INVENTION

This invention relates to the field of antigen presentation for the activation and resultant induction of antigen-specific immune responses and the inhibition of viral replication by the formation of "Biological Carriers."

BACKGROUND OF THE INVENTION

In mammals, antigen-presenting cells (APCs) process foreign antigens. The processing of the antigen within the APC triggers an efficient immune response within the host. Antigens are degraded into peptide fragments and become bound to major histocompatibility complex (MHC) molecules that are expressed on the cell surface and are able to interact with other cells of the immune system. Dendritic cells, macrophages, and Kupffer cells in the liver are among the most commonly encountered type of APCs. These cells readily engulf foreign particles and express MHC molecules on their plasma membrane surface. These MHC surface molecules, know as human leukocyte antigens (HLA) in humans, are involved in the immune response against disease.

There are two classes of MHC molecules (class I and class II). MHC class I molecules display exogenous antigens (i.e., antigens taken up from outside the cell), whereas MHC class II molecules display endogenous antigens (i.e., antigens that originate within the cell) to the immune system. Processing of the antigens differ in each case. Processing of exogenous antigens by APCs occurs in stages. The cells first take up the antigens by endocytosis. The internalized endocytic vesicles then fuse with lysosomes where the foreign antigens are hydrolyzed by lysosomal enzymes, resulting in peptide fragments of 10 to 20 amino acids. These peptide fragments bind to a cleft within the MHC molecule and are transported to the cell's surface for interactions with cells of the immune system. The processing that leads to the display of endogenous antigens can arise from viral infection, etc. Such antigens are cleaved in the cellular cytosol, and transported into the lumen of the endothelial reticulum, where they become associated with MHC class I molecules, which are then transported to the cell surface. Foreign antigens can promote an immune response, whereas peptide fragments derived from cellular proteins when bound to MHC class I molecules and presented on the cell's surface are recognized as "self" and will not usually elicit an immune response.

Processed antigens displayed on self-MHC molecules supply one of the two signals required for T-lymphocyte activation. In addition to recognition of a foreign antigen fragment, simultaneous delivery of a co-stimulatory signal is needed for the activation of naïve T-lymphocytes. These co-stimulatory signals together with both class I and class II MHC molecules are molecules present on professional APCs. The presence of these molecules on professional APCs stimulate the clonal expansion of naïve T-lymphocytes, resulting in their differentiation into armed immune effector cells, and ultimately memory cells. Priming is a process where naïve T-lymphocytes are activated by the first time exposure to an antigen, whereas re-exposure to foreign antigens result in activation of memory cells.

Activation occurs when the T-lymphocyte's T cell receptor (an antigen-specific receptor) and its co-receptors (either CD4 or CD8 molecules) recognize the foreign peptide-MHC complex, simultaneously with a co-stimulatory signal delivered from the same APC. The best-characterized co-stimulatory molecules on APCs are CD80 (B7-1) and CD86 (B7-2). These structurally related molecules are members of the immunoglobulin superfamily and recognize the CD28 molecule on T-lymphocytes, resulting in T-lymphocyte activation. Activation of T-lymphocytes is controlled by the subsequent expression of CTLA-4. The CTLA-4 receptor is closely related to the CD28 molecule that binds the B7 molecules with a higher affinity than CD28 and prevents further T-lymphocyte activation.

There are numerous examples of how the addition of co-stimulatory molecules to cells affects cellular processes. In HIV/AIDS research: When CD3 and CD28 receptors on cultured T-lymphocytes are stimulated by immobilized monoclonal antibodies (mAbs), expansion of polyclonal CD4 positive T-lymphocytes occur. If the T-lymphocytes were obtained from FIV-infected donors, HIV-1 viral load declines (in the absence of antiretroviral agents) simultaneously with T-lymphocyte expansion. Moreover, CD28 stimulation rendered these cells highly resistant to HIV-1 infection, mediating an antiviral effect early in the viral life cycle before HIV-1 DNA integration. The HIV-1 resistant state is specific for the macrophage-tropic HIV-1 isolates and is due to the lack of CCR5 receptor transcription, which is a required secondary receptor for HIV-1 macrophage-tropic virus infection. In tumor biology: The introduction of either MHC class II molecules or co-stimulatory molecules to tumor cells results in their efficient rejection in vivo. In virology: Viral infection with a number of the herpesviruses causes a diminution of cell surface co-stimulatory molecule expression, resulting in viral replication without mounting any immune response towards the infected cells.

Many viruses produce degenerative changes in cells when replicating in a susceptible cell culture. These characteristic changes are called cytopathic effects and are associated with certain morphologic changes in the host cell. The intracellular sites where the events of viral replication take place vary among the viral families. Enveloped viruses mature by a budding process, although some budding occurs with non-envelope containing viruses. For envelope viruses, viral-specific envelope glycoproteins are inserted into cellular membrances and the viral nucleocapsids then bud through the membrane at these modified sites. In this process, the virus acquires their envelope for infectivity and can also acquire cellular-related molecules. Studies with HIV, Influenza, and Chlamydia have shown virus particles that have incorporated HLA molecules into the mature virus particle. During the infection the cell is destroyed and the virus particles are released into the culture supernatant. The amount of infectious virus present in the cell culture fluid can be titrated and infectivity inactivated by a variety of methods. Although inactivated virus particles have lost the ability to replicate they maintain their structure, as detailed in this application, they can be used as a scaffold to carry cell surface expressed molecules.

SUMMARY OF THE INVENTION

This invention provides for the formation of non-infectious Biological Carrier to deliver signals to cells either in vitro or in vivo (see FIG. 1A). The Biological Carriers are whole virus particles that are either totally inactivated (by biological, chemical, genetic or mechanical means), or partially inactivated for subsequent viral infection. They are produced in cells that are genetically modified to over-express surface molecules that are able to elicit immune responses (see FIG. 1B for concept in schematic form). The invention is intended for in vivo use in any recipient where enhancement of immune responses can be advantageous to that individual, although in vitro pretreatment of cells can also be envisioned.

Viruses are ideal candidates for utilization as non-professional antigen presenting carriers. The invention uses viruses not for their infectious abilities (all preparations will be inactivated), but as a scaffold that contain specific antigens and co-stimulatory molecules to induce immune responses. The major advantage of this approach is the ease of production of potential therapeutic and/or vaccine doses. At the end of the virus life cycle, large amounts of virions are released from infected cells, reaching concentrations of $10^{12}$ virus particles per milliliter of culture fluid. Intrinsic to virus release, portion of the cell membrane are removed as the mature virus particle buds from the cell. The cells that support the productive viral infection can be genetically engineered to over-express surface molecules that would be carried with the virus particle as it is released from the cell. In addition, MHC class I and class II molecules containing viral peptides (due to the active viral infection) will decorate the virus particles, thereby presenting the antigens needed to stimulate the CD3 receptor on T-lymphocytes. These interactions supply one of the two signals required for T-cell stimulation. The over expression of co-stimulatory molecules by genetic engineering supplies the second signal, leading to antigen specific immune stimulation. These are distinct advantages over the use of cells (professional or non-professional) to present antigens to T-lymphocytes. The current procedure with professional antigen presenting cells (APCs) involves isolating cells from a patient, growing them in culture, and transplanting them back into that same person, a process that takes weeks. With non-professional APCs, a genetic engineering step (where co-stimulatory and/or MHC molecules would be introduced into the cell) would be added to the process. Even if the cells can be implanted allogeneically, current procedures are cumbersome, labor intensive, time consuming, and expensive. The present invention simplifies the process, thereby making immunotherapy potentially available world-wide in the area of infectious diseases.

In one aspect, the invention provides a Biological Carrier preparation that (i) contains an antigen (here, the antigen can be a protein, polypeptide, lipid or glycolipid) and/or antigen fragment bound to a primary surface molecule of said host cell such that the Biological Carrier contains at least one antigen fragment presented to initiate an immune response and (ii) at least one co-stimulatory molecule. In one embodiment of this aspect, the Biological Carrier preparation is virus-specific. That is, a specific virus is grown in a fully permissive cell line and while budding from the cells' surface contains at least one antigen specific to that virus processed into an antigen fragment. The Biological Carrier preparation can be prepared by infection of a permissive host cell line (or primary cell), from a chronically infected cell line, from a packaging cell line (a cell engineered to express a virus particle capable of one replicative infectious cycle), or from cells isolated directly from the mammal (cells isolated from the tumor or of non-tumor source). In addition, the Biological Carrier preparation can be from the native harvested culture fluid, or the preparation can be concentrated (e.g. centrifugation, polyethylene glycol-precipitation, or the like) and/or lyophilized for ease of storage and stability. In another embodiment, the Biological Carrier preparation also contains a non-specific immune stimulatory activity. That is, molecules are expressed at the cell's surface that would indiscriminately stimulate T-lymphocytes. Such molecules can be a stimulatory antibody directed against the T-lymphocyte CD3 molecule, but not limited to this molecule, and when the virus buds from the infected viral cells' surface it contains in addition to at least one viral specific antigen processed into an antigen fragment, also a non-specific molecule that can enhance immune responses in the recipient. Preferably, these viral-specific antigens are in a form available for presentation. Further, the Biological Carrier preparation contains at least one co-stimulatory molecule. Preferably the co-stimulatory molecule is cell surface associated and in a form available for presentation. The primary surface molecules for antigen presentation are preferably MHC I, MHC II or CD1. The co-stimulatory molecule is preferably selected from the group consisting of CD80 and CD86, but not restricted to this group of molecules.

In another aspect, the invention provides a method for stimulating the presentation of at least one exogenous antigen fragment on the Biological Carrier, which method comprises contacting a virally infected cell that is capable of expressing at least one co-stimulatory molecule along with (i) an endogenous viral antigen (one intrinsic to the viral infection), (ii) an exogenous antigen (one important in initiating an immune response), (iii) an immune dominate peptide (one loaded onto the MHC molecule before or during virus expression). This exogenous antigen can be included in vitro in the culture media where it would be taken up by the virus host cell or can be supplied as genetic material that codes for the exogenous antigen, which the cell processes intracellularly into at least one antigen molecule or fragment. The method can further include contacting the virally infected cell with cytokines (such as tumor necrosis factor-alpha) or by contacting with other reagents (phorbol esters), during the production of the Biological Carriers in order to enhance, stimulate or induce virus expression.

In another aspect, the invention provides a method of activating or priming a naïve T-lymphocyte to respond to viral antigens, by contacting the T-lymphocyte with a Biological Carrier preparation containing either viral-specific antigen(s) fragments or with non-specific immune activators in the proper conformation for presentation. In addition, the Biological. Carrier may contain at least one co-stimulatory molecule. This T-cell priming can allow for the induction and expansion of not only effector cells but also long-lasting memory T-lymphocytes against a specific virus.

In another aspect the invention provides a Biological Carrier preparation, which expresses at least one membrane bound exogenous antigen and/or antigen fragment and also expresses a co-stimulatory molecule. Thus, the Biological Carrier preparations contain the antigen and/or antigen fragment available to "professional" APCs for their processing and presentation to T-lymphocyte. In one embodiment of this aspect, the Biological Carrier preparation has been contacted with at least one antigen fragment (either exogenous or endogenous), which the viral infected cell displays on its cell surface. In another embodiment, the Biological Carrier contains at least one antigen fragment obtained from the introduction of exogenous genetic material into the viral host cell. Preferably this exogenous genetic material is in an expression vector. Further, the Biological Carrier preparation also contains exogenous genetic material that codes for at least one co-stimulatory molecule. Preferably, this exogenous genetic material is also in an expression vector.

In another aspect, the invention further provides a method for determining the immune competence or state of activation of the T-lymphocyte population of a mammalian host to a particular class of antigens by contacting the T-lymphocyte population with a specific biological preparation and observing for any change in the state of activation (e.g. Alamar-Blue fluorescence, T-lymphocyte production of gamma interferon, or expression of T-lymphocyte surface activation markers).

The present invention further relates to the treatment or prevention of a disease in a mammal, which may be a human or non-human, by administering to the mammal a Biological Carrier preparation that (i) contains at least one viral-specific antigen bound to a primary surface molecule that can be presented to initiate an immune response and (ii) also contain at least one co-stimulatory molecule (e.g., B7-1 and/or B7-2). In one embodiment of this aspect of the present invention, the Biological Carrier contains at least one processed viral antigen. In another embodiment, the Biological Carrier preparation contains at least one processed, but exogenously added viral antigen. Such mechanisms of prevention and/or treatment in mammals have application with respect to various diseases (whether viral, bacterial, fungal, or other origin), cancer, toxin exposure (whether viral, bacterial, fungal, or other origin), or antigens of plant origin (e.g. poison ivy, poison sumac), and the like.

In summary, the Biological Carrier preparation system has a wide range of applications, including but not limited to, in vitro or in vivo activation and expansion of antigen specific T-lymphocytes for use in adaptive cellular immunotherapy against infectious diseases and cancer, for use of Biological Carrier preparations for vaccines and/or immunotherapeutics, and for an in vitro assay system for determining an individual's immune potential or potentiation to any antigenic epitopes. The present invention provides a method to form non-infectious Biological Carrier to deliver signals to cells either in vitro or in vivo. The Biological Carriers of the present invention are inactivated virus particles that have been specifically modified to exhibit biological properties that differ from those of virus particles deriving from an unmodified host cell. The modified cell that is host to the virus (i) expresses at least one co-stimulatory molecule and (iia) at least one antigen that can initiate an immune response, and/or (iib) express surface molecules that suppress viral replication. The co-stimulatory molecule is one of a class of molecules that either alone or in combination with other molecules is capable of T-lymphocyte stimulation leading to specific antibody formation and/or cytotoxic T-cell activity in the host. Specificity is conferred to the Biological Carrier by the presence of endogenous and exogenous processed antigens that are bound to Class I and Class II major histocompatibility complex (MHC) surface molecules that are present on the modified cell. Processed antigens can be intrinsic to the infectious process or disease specific antigens from said host cell. Also disclosed is a method for inhibiting viral replication by stimulating cells with Biological Carriers containing molecules that stimulate specific receptors that are present on human peripheral blood mononuclear cells that are able to prevent viral entry. Thus, disclosed are methods for the treatment or prevention of a disease in mammals including humans.

The present invention particularly concerns:

1. A method for inducing an antigen-specific T-cell response in a mammal comprising administering to the mammal an effective amount of a Biological Carrier preparation that has been derived from a host cell that contained at least one fragment of said antigen bound to a primary surface molecule of said host cell, and which also expressed at least one co-stimulatory molecule, said molecules being carried on the Biological Carrier preparation and inducing an immune response against the specific antigens that were processed in said host cell.

2. A method to inhibit viral replication and/or viral entry in a mammal comprising administering to the mammal an effective amount of a Biological Carrier preparation that has been derived from a host cell that contained at least one molecule either alone or in combination with one or more other molecules expressed on said host cell, said host cell expressing one or more molecules that prevent expression of molecules required for viral entry, said molecules required for viral entry being carried on the Biological Carrier preparation leading to an inhibition of viral replication.

BRIEF DESCRIPTION OF THE DRAWINGS

The invention is further described by the accompanying drawings and the description thereof herein, although neither is a limitation of the scope of the invention.

FIG. 1B) schematically represents formation of the carrier particles.

FIG. 2 shows that when Biological Carriers (either HSV-2 or HIV-1 based) are produced from untransduced host cells the degree of relative fluorescence (a measure of lymphocyte activation) is similar to unstimulated cultures. PHA-stimulated cultures were included to show that the cells were capable of stimulation as measured by the Alamar-Blue fluorescent assay. Values were from day 6 cultures.

FIG. 3, Panel B shows the comparative stimulatory activity of HSV-2 based Biological Carriers prepared from untransduced (Un), anti-CD3 (A), B7-1+B7-2 (B), and anti-CD3+B7's (A+B) on elutriated peripheral blood lymphocytes after 14 days in culture.

FIG. 10 shows the effects of exposing elutriated lymphocytes to HSV-2 based Biological Carrier preparations. Unlike the HIV-1 based Biological Carrier treatment shown in FIG. 9, HSV-2 based Biological Carrier treatment did not inhibit HIV-1 replication. This data attests to the specificity of the Biological Carrier preparations. The preparations show specificity only towards the virus used to prepare the Biological Carrier preparation. This experiment used Donor #9 elutriated lymphocytes and was done at the same time as the experiment in FIG. 9.

DETAILED DESCRIPTION OF THE PREFERRED EMBODIMENTS

Figure 1A:
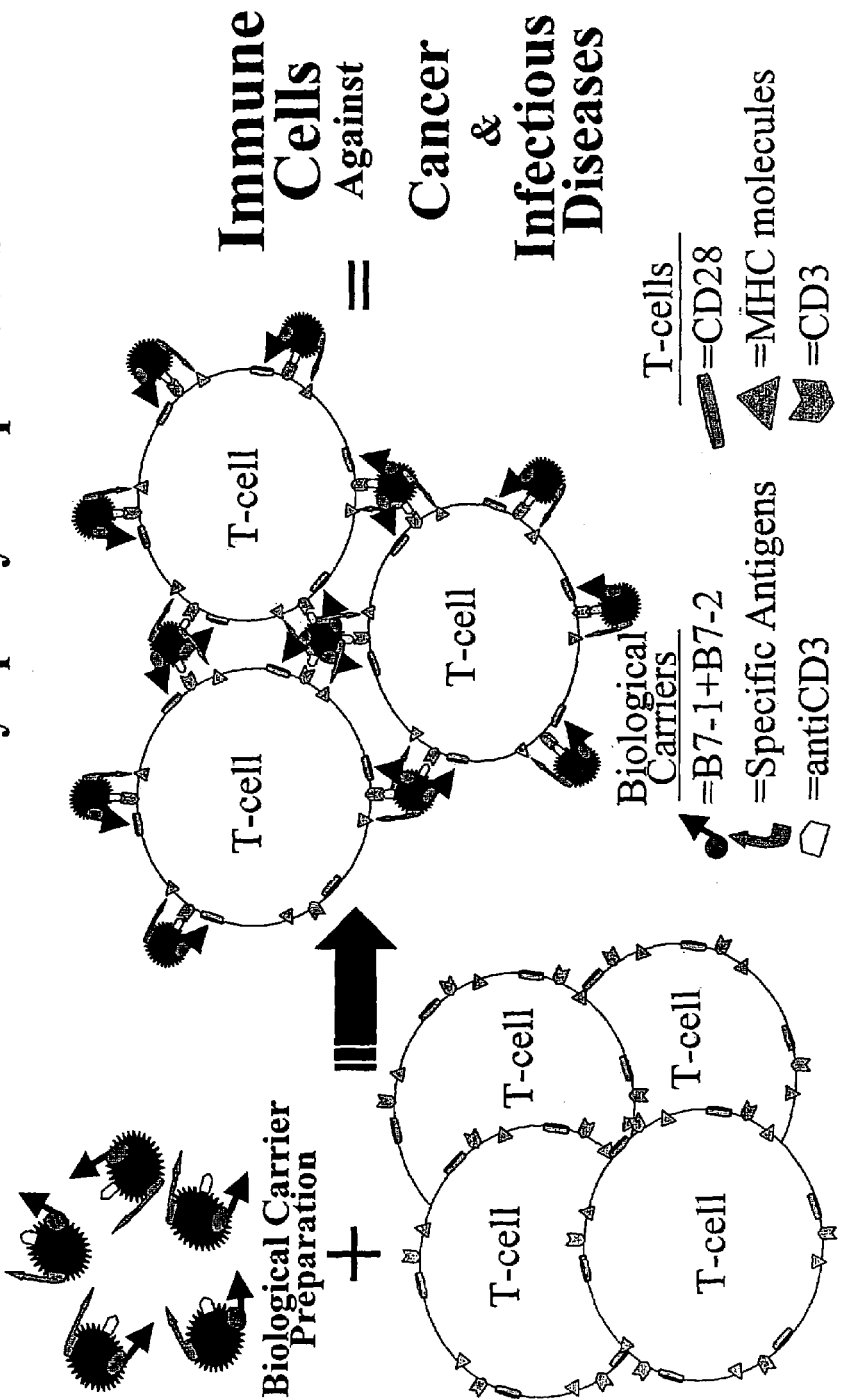
FIG. 1A is an illustration of the interaction of the Biological Carrier preparations with dormant T-lymphocyte populations, resulting in their activation and induction of specific immune responses.

The present invention relates to the expression of surface molecules on constructed cell lines that are host to specific viruses or viral-like particles. The virus may contain either a DNA or RNA genome, or be composed of material that induces a budding process from cells. The expressed surface molecules can be endogenous to the cell line selected, or can be specific for one or more molecules expressed on the surface of a given cell by biological, chemical, or mechanical means. The surface molecule can be naturally expressed in nature on a cell's surface, or can be engineered as such by molecular, chemical, or mechanical means. The cell lines can be chronically-infected with the virus or the virus can be introduced into the cell by biological, chemical, or mechanical means. The formation of the budding particle containing native (those surface molecules naturally present on said cell surface) and/or specific molecules (those surface molecules that were intentionally introduced on said cell surface) is used as a carrier (referred to herein as a "Biological Carrier") of that material for the purpose of signaling or modifying specific cellular events.

The present invention relates to, but is not limited to, antigen presentation leading to the activation of immune responses. Immune responses can be specific expansion or activation of one or more cell populations. The "Biological Carriers" can behave as antigen-presenting cells for the activation of T cell responses, or as an in vitro method for assessing immune responsiveness to specific infectious disease agents. The present invention provides for use of "Biological Carriers" to present relevant antigens and appropriate co-stimulatory molecules as an immunoprophylactic, immunotherapeutic, or vaccine candidate to treat, for example, infectious diseases, cancer, exposure to toxins, and as an alternative to conventional drug and/or antibiotic therapies on which host resistance has developed. Pursuant of the present invention, both HSV-2 and HIV-1 were chosen as an example of a DNA and RNA virus, respectively. However, any virus including but not limited to or inducing a budding process that incorporates membrane fragments into a scaffold particle can be used to generate a Biological Carrier. Each Biological Carrier preparation was prepared from untransduced, anti-CD3-transduced, or B7-1+B7-2 transduced with and without anti-CD3 and data was presented to demonstrate the ability of the transduced cells to activate T-lymphocytes. Although the transduction of specific surface molecule expression may generally be desired, in some cases, whether it is due to the cells selected or to the virus being used, appropriate molecules or nuances related to the viral life cycle may eliminate the need for virus host cell surface modifications. The invention is further envisioned as a general way of delivering molecules to humans in vivo. The forced surface expression of molecules that are normally secreted or sequestered internally within cells, when expressed in the context of a "Biological Carrier" is anticipated to display increased stability from degradation resulting in longer and/or enhanced biological activity. Genetic engineering of molecules for surface expression and ultimately displayed on the surface of the "Biological Carrier" can include (in addition to molecules that would interact with cellular receptors on the responding cell) molecules whose mode of action require entry internal to the cell Internalization can be receptor-mediated or mediated through biological or chemical modifications that allow passage across the cell's outer and/or nuclear membranes. In the present embodiment, all "Biological Carrier" preparations will be inactivated thereby not allowing for viral replication. However, in some instances partially inactivated, or non-inactivated, preparations might be envisioned.

The "Biological Carriers" described herein establish an ideal system for assessing the ability of human patients to respond immunologically by testing their T-lymphocyte responses. By assessing an individual's immune competency, the ability to respond to a particular vaccine can be determined, in addition the ability of an individual can be pre-screened to be responsive to a specific "Biological Carrier" preparation before receiving the material in order to determine the potential benefit of the administration. The potent accessory cell function of the "Biological Carriers" may be able in vivo to present infectious disease agents and/or tumor antigens to T-lymphocytes obtained from afflicted individuals, whose immune response apparently is inadequate to mount an effective response to eliminate the infectious agent or tumor. In addition to the in vivo expansion of effective T-lymphocytes, activated T-lymphocytes can be expanded in vitro for use in immunotherapeutic applications. Tumor cells isolated from patients or established tumor-derived cell lines can be used as host for virus infections. The virus used in this manner can be related to the tumor in question or can be from, or be derived from, a separate group of viruses that are permissive to grow in said tumor cells for the expressed purpose of budding and thereby removing tumor specific antigens already processed in the proper configuration for T-lymphocyte presentation. These tumor cells can be in addition modified on their cell surface with co-stimulatory molecules or other accessory molecules that would facilitate the "Biological Carrier's" ability to mount an immune response against the tumor.

Infectious disease agent against which the present invention may be applicable in the induction of an immune response include but are not limited to bacteria, parasites, fungi, and viruses. The multitudes of antigens encoded by these agents that may be processed and presented by the "Biological Carriers" include but are not limited to external surface proteins and structural proteins including intracellular enzymes, transcription factors, and other cell regulatory proteins. For example, antigens encoded by any genes of the HIV-1 genome including gag, pol, vif vpu, tat, rev, env, and nef may be all present as either intact antigens or processed and configured within the MHC molecule as part of the "Biological Carrier" for either presentation of the intact antigens to "professional" antigen presenting cells (macrophages, dendritic cells, etc.) or directly to T-lymphocytes, respectively. In addition, a variety of other infectious agents including hepatitis B, hepatitis C, herpes simplex virus, varicella zoster, Epstein-Barr virus, cytomegalovirus, human herpesvirus-6, -7, -8, HIV-1, HIV-2, HTLV-1, HTLV-2, Rubella, Rubeola, Influenza, and species of Chlamydia, Helicobacter, Neisseria, Mycobacteria (especially *M. tuberculosi*) and Toxoplasma are encompassed within the scope of the invention. The antigen(s) can be present on the host cell either as part of the infectious processed, naturally native to the cell, or introduced by pinocytotic uptake, or by biological (viral vectors), chemical (liposomes), or mechanical (electroporation) methods.

The following examples further illustrate experiments using Biological Carrier preparations that have demonstrated reduction to practice and utility of selected preferred embodiments of the present invention, although they are in no way a limitation of the teachings or disclosure of the present invention as set forth herein.

EXAMPLE 1

Requirement for Host Cell Modification(S) for Biological Carrier-Dependent Lymphocyte Stimulation The principle of this invention is demonstrated by proliferation experiments comparing the degree of stimulation of biological carrier preparations obtained from untransduced, anti-CD3, B7-1+B7-2, and anti-CD3&B7-1+B7-2 transduced cultures.

Figure 3:
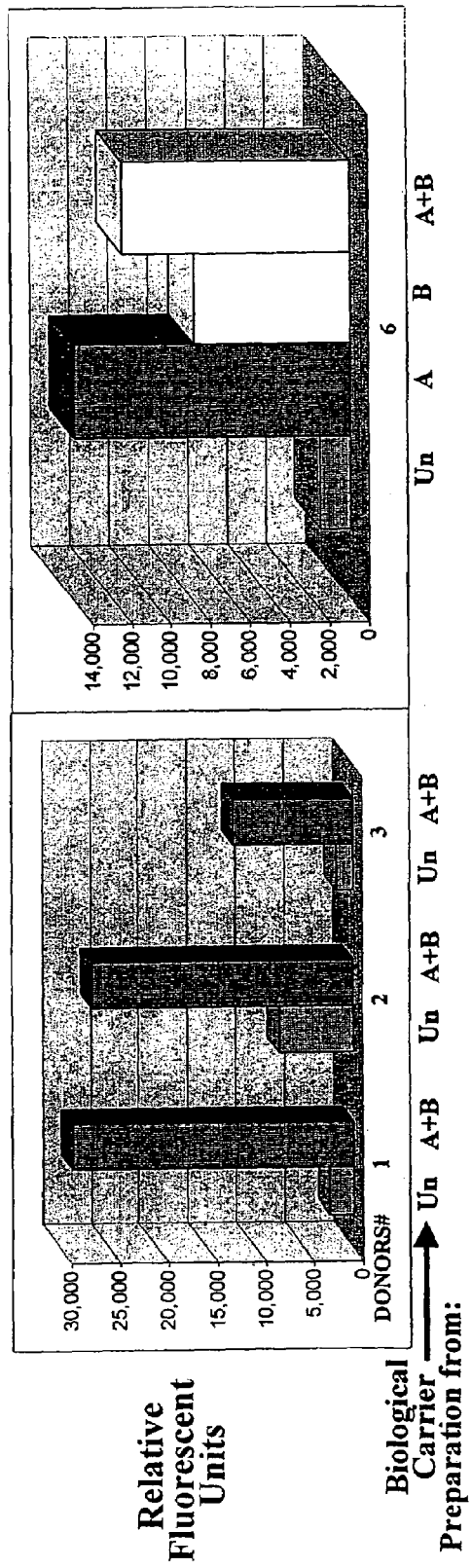
FIG. 3, Panel A shows the stimulatory ability at day 6 of HSV-2 based Biological Carriers prepared from anti-CD3+B7's transduced cultures (A+B) to stimulate T-lymphocytes compared to HSV-2 based Biological Carriers prepared from untransduced cultures (Un) in three different donor lymphocyte preparations.
Figure 4:
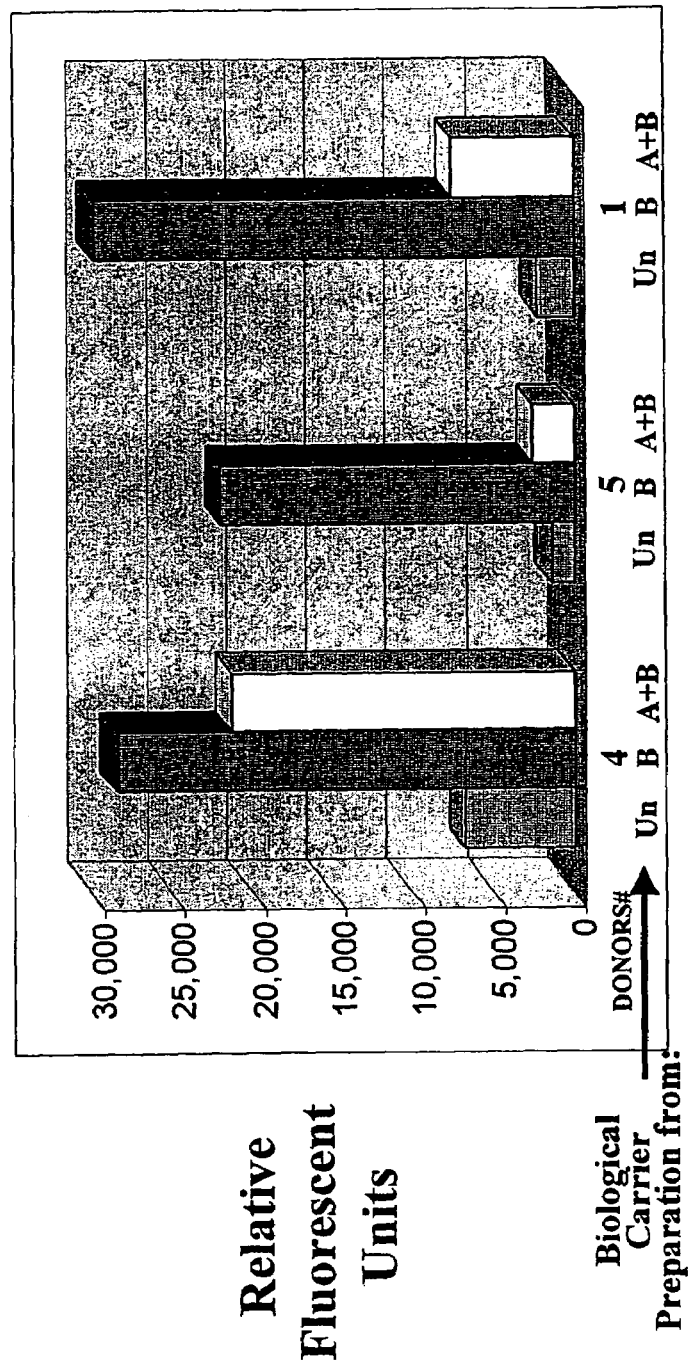
FIG. 4 shows the stimulatory ability at day 6 of HIV-1 based Biological Carriers prepared from either B7-1+B7-2 (B−) or anti-CD3+B7's (A+B) transduced cultures to stimulate lymphocytes compared to HIV-1 based Biological Carriers prepared from untransduced cultures (Un) in three different donor peripheral blood lymphocyte preparations.

Elutriated lymphocytes that were treated for six day with a preparation of biological carriers obtained from untransduced cultures showed a degree of proliferation (lymphocyte stimulation) similar to unstimulated (un-treated) cells (FIG. 2). Proliferation was measured by AlamarBlue™ assay. The assay is designed to measure quantitatively the proliferation of human cells by the incorporation of an oxidation-reduction indicator that fluoresces in response to chemical reduction of growth medium resulting from cell growth. The lack of biological carrier dependent stimulation when biological carriers were prepared from untransduced cultures was independent of the virus used to form the biological carrier particles. Both HSV-2 and HIV-1 based biological carriers prepared from untransduced host cells failed to stimulate the lymphocyte proliferation. The host cell for the HSV-2 based biological carriers are Lof(11-10) cells (an SV40 T-antigen transformed stromal cell line that was infected with HSV-2), whereas the host cells for the HIV-1 based biological carriers are 1119ERC cells (a chronic HIV-1 infected cell line established by the electroporation of pHXB2 that contains the HIV genome into A3.01 cells). The introduction of genetic material coding for either or both anti-CD3 and B7-1+B7-2 was accomplished by MuLV-based retroviral transduction and selection of the cells that incorporated and expressed said molecules. The data from PHA stimulated cultures was included in FIG. 2 to show that the elutriated lymphocytes were capable of fluoresces in response to known proliferating compounds. However, HSV-2 based biological carriers prepared from either anti-CD3&B7-1+B7-2 transduced cells in three different donor's lymphocytes (FIG. 3, panel A) or anti-CD3, B7-1+B7-2, and anti-CD3&B7-1+B7-2 transduced cells in a fourth donor's lymphocytes (FIG. 3, panel B) was able to stimulate T-lymphocyte proliferation. T-lymphocyte stimulation was also observed in three different donor's T-lymphocyte populations when exposed to HIV-1 based biological carriers obtained from B7-1+B7-2 and anti-CD3&B7-1+B7-2 transduced cells, but not from untransduced cultures (FIG. 4). The identity of the donor T-lymphocytes and the key for the abbreviations used in the Figures are listed in Table 1.

EXAMPLE 2

Biological Carrier Preparations Retain Their Biological Activity After Lyophilization and Storage at Room Temperature The principle of this invention is further demonstrated by retention of cellular proliferating biological activity when biological carrier preparations were lyophilized and stored at ambient temperatures.

Figure 5:
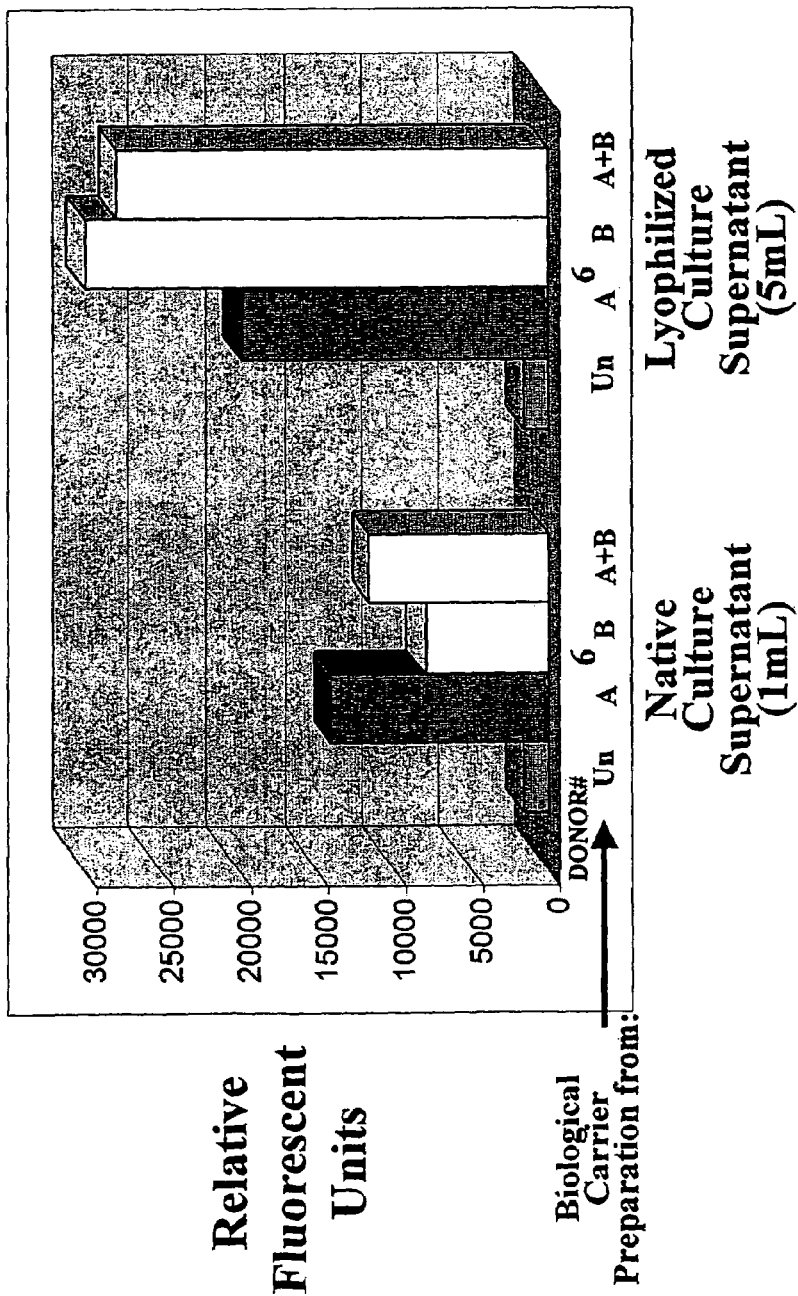
FIG. 5 shows the ability of lyophilized HSV-2 based Biological Carrier preparations from anti-CD3 (A), B7-1+B7-2 (B), and anti-CD3+B7's (A+B) transduced cultures to stimulate lymphocytes compared to the same preparation that was not lyophilized after 13 days in culture. The enhanced stimulation in the case of the lyophilized preparation is probably due more to the larger volume (5 mL) of native culture supernatant lyophilized and tested in the experiment than to the lyophilized procedure itself.

The ability of native harvested culture fluid from HSV-2 based biological carriers from anti-CD3, B7-1+B7-2, and anti-CD3&B7-1+B7-2 transduced cells were compared to aliquots of the same sample fluids after lyophilization with respect to the ability of the preparations to stimulate T-lymphocytes in culture. In addition to lyophilization, the lyophilized material was stored at room temperature for two weeks before testing biological activity. After thirteen days in culture with Donor #6 T-lymphocytes (Table 1), the lyophilized culture supernatant from the transduced host cells showed similar stimulation of proliferation to that observed with the native culture supernatants (FIG. 5).

TABLE 1

List of Donor Cells and Key for Biological Carrier Preparations

Donors:

1 = Lot#0G0002 Elutriated lymphocytes
2 = Lot#0G0008 Elutriated lymphocytes
3 = Lot#0H0005 Elutriated lymphocytes
4 = Lot#0J0009 Peripheral Blood Mononuclear Cells:
5 = Lot#0J0019 Elutriated lymphocytes
6 = Lot#0H0015 Elutriated lymphocytes
7 = Lot#0H0014 Elutriated lymphocytes
8 = Lot#0H0027 Elutriated lymphocytes
9 = Lot#1A0008 Elutriated lymphocytes Biological Carrier Preparations: Un (Untransduced Cultures); B (B7-1 + B7-2 transduced); A (Anti-CD3 transduced) A + B (AntiCD3 + B7's Transduced Cultures)

Table 1 lists the nine different donors cells used in the data presented in the following Figures. Eight of the nine cell preparations were obtained by elutriation of human peripheral blood mononuclear cells and are depleted of monocytes. Donor #4 consists of ficoll-fractionated peripheral blood. In addition, Table 1 gives the meaning for the abbreviations Un, A, B, and A+B that refer to the host cell used to prepare the Biological Carrier preparations.

EXAMPLE 3

Biological Carrier Preparations Retain Their Biological Activity After Concentration The principle of this invention is further demonstrated by retention of cellular proliferating biological activity when biological carrier preparations were concentrated.

Figure 6:
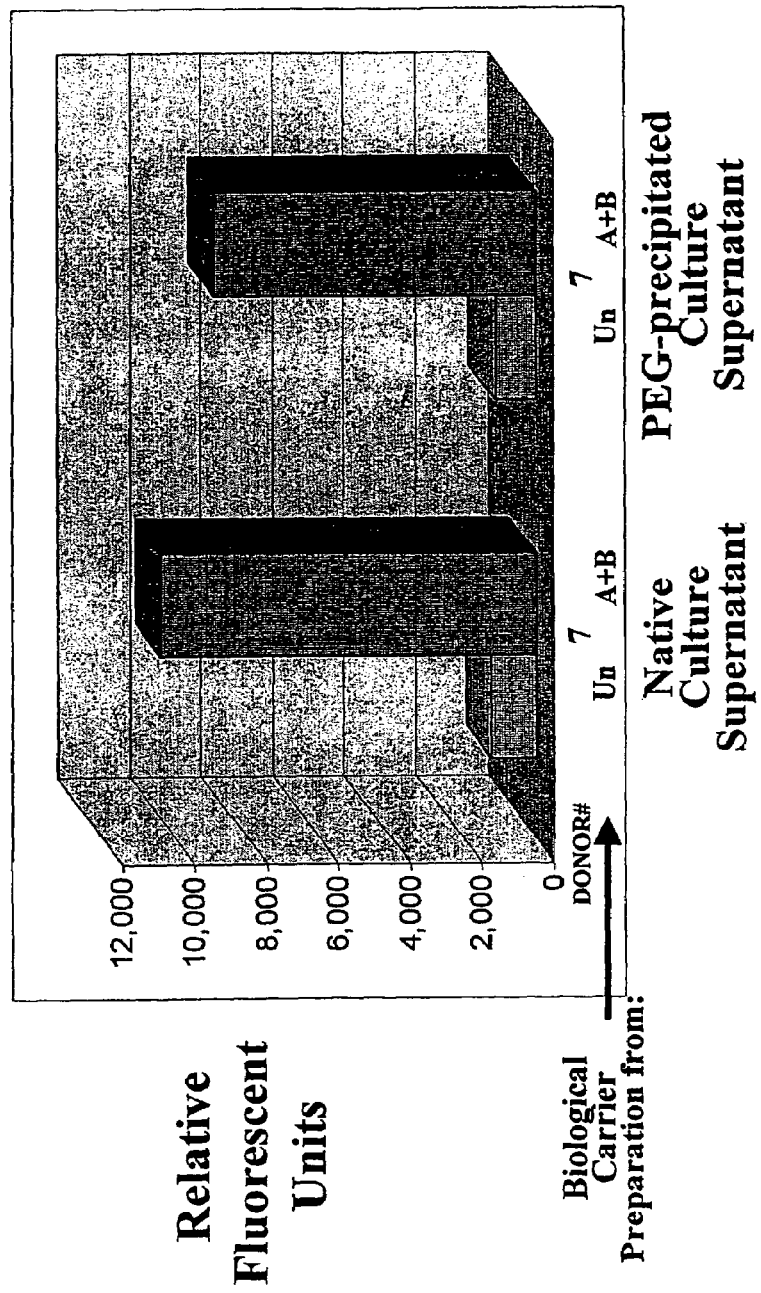
FIG. 6 shows that the concentration of the native culture supernatant (by polyethylene glycol precipitation) maintains the stimulatory activity of the HSV-2 based Biological Carriers obtained from anti-CD3+B7's transduced cultures. This was a 40-fold concentration, allowing smaller volumes (25 μL rather than 1 mL) of the preparation to be used to obtain similar effects. The time point shown is 10 days after the addition of Biological Carriers.

The ability to stimulate T-lymphocytes with native harvested culture fluid from HSV-2 based biological carriers obtained from untransduced or anti-CD3&B7-1+B7-2 transduced cells were compared to the same supernatants concentrated by polyethylene glycol (PEG) precipitation. The addition of PEG to culture fluid results in the formation of a precipitate. Virus (HSV-2) infected harvested culture supernatants were centrifuged at 4,000 times the force of gravity for 10 minutes, removing large particulate material from the culture fluid. Polyethylene glycol was added to the clarified supernatant to 6% and after 4 to 16 hours of incubation at 4° C. a precipitate was collected by centrifugation. Following resuspension of the pellet (40× concentrate), the material was compared to the native culture supernatant in T-lymphocyte proliferation assay. The PEG biological carrier material from transduced cultures stimulated T-lymphocyte proliferation similar to the unprocessed biological carrier preparations (FIG. 6).

EXAMPLE 4

T-Lymphocytes Stimulated with Biological Carrier Preparations can Undergo a Second Stimulation when Re-Exposed to the Same Biological Carrier Preparation The principle of this invention is further demonstrated by observing secondary responses to re-administering the biological carrier preparation to the same population of cells.

Figure 7:
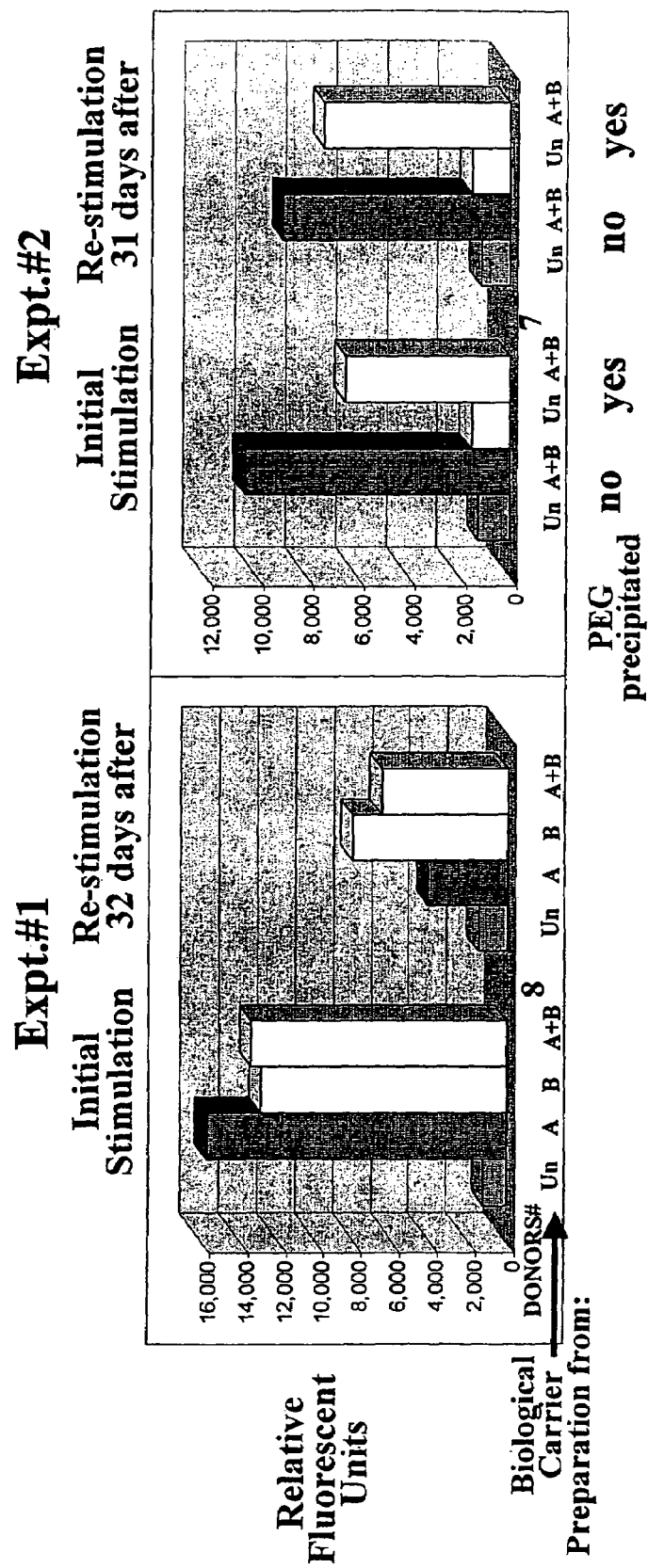
FIG. 7 shows that the lymphocyte response can be re-activated in the same cultures that where initial stimulated even after the lymphocytes were rested for over one month in culture. The Figure shows two experiments with two different donors. Experiment 1 used native culture supernatants for the initial stimulation and re-stimulation; experiment 2 used polyethylene glycol precipitated culture supernatants for the initial stimulation and re-stimulation. Note that the initial stimulation in experiment 2 is the same as the experiment shown in FIG. 6.

Two donor lymphocytes, #8 and #7 in experiment #1 and #2, respectively, were initially stimulated with untransduced and transduced (anti-CD3, B7-1+B7-2, and anti-CD3&B7-1+B7-2) HSV-2 based biological carrier preparations (FIG. 7). The data shown for the initial stimulation was 7 days after exposure of the cells to the biological carrier preparation. By 14 days there was no observed fluorescent activity over the untransduced cultures (data not shown). These cultures were kept in this resting state for 32 days in experiment #1 and 31 days in experiment #2. After which the cultures were re-exposed to the same biological carrier preparation used in the initial stimulation. The ability of the cultures to show a proliferative response to re-administration of the biological carrier preparation suggests that the biological carrier preparations can be used therapeutically to control and maintain immune responses.

EXAMPLE 5

Figure 8:
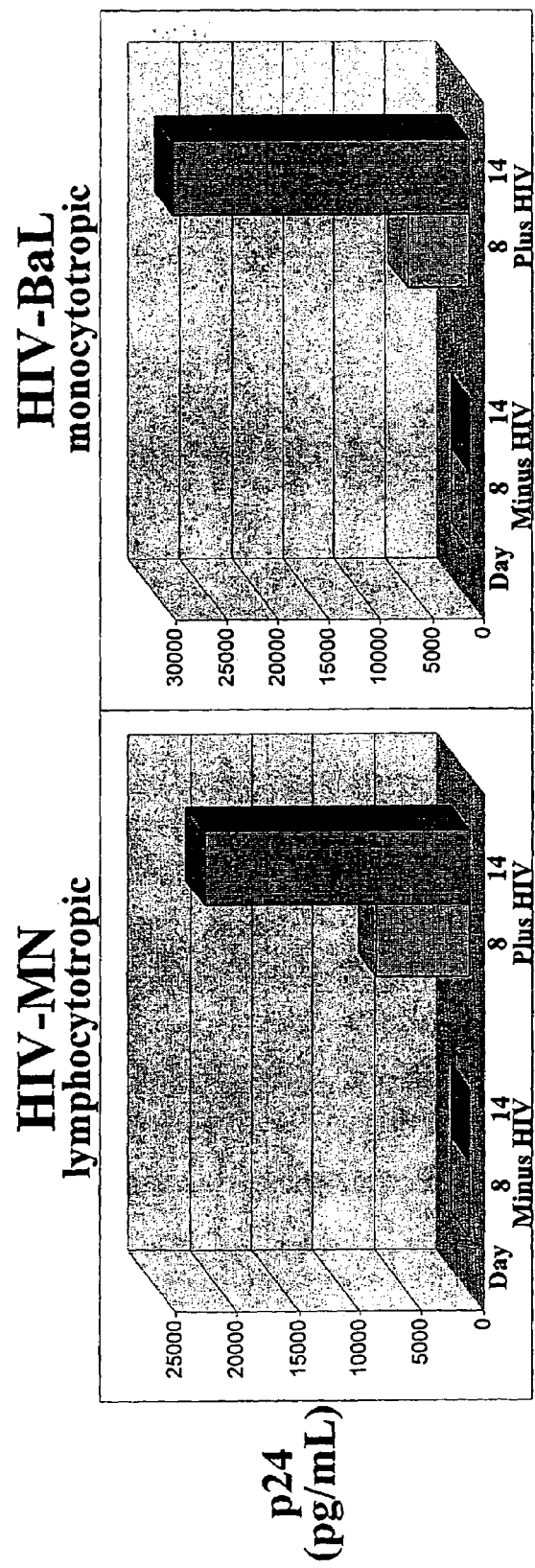
FIG. 8 shows the increase in HIV-1 encoded p24 antigen expression after exposure of elutriated T-lymphocytes to either HIV-MN (a lymphocytotropic HIV strain) or HIV-BaL (a monocytotropic HIV-1 strain). Although each HIV strain requires a different secondary receptor for cellular entry (CCR5 for monocytotropic strains and CXCR4 for lymphocytotropic strains) the viral strains used are replication competent in these cells. This experiment used Donor #9 elutriated lymphocytes.
Figure 9:
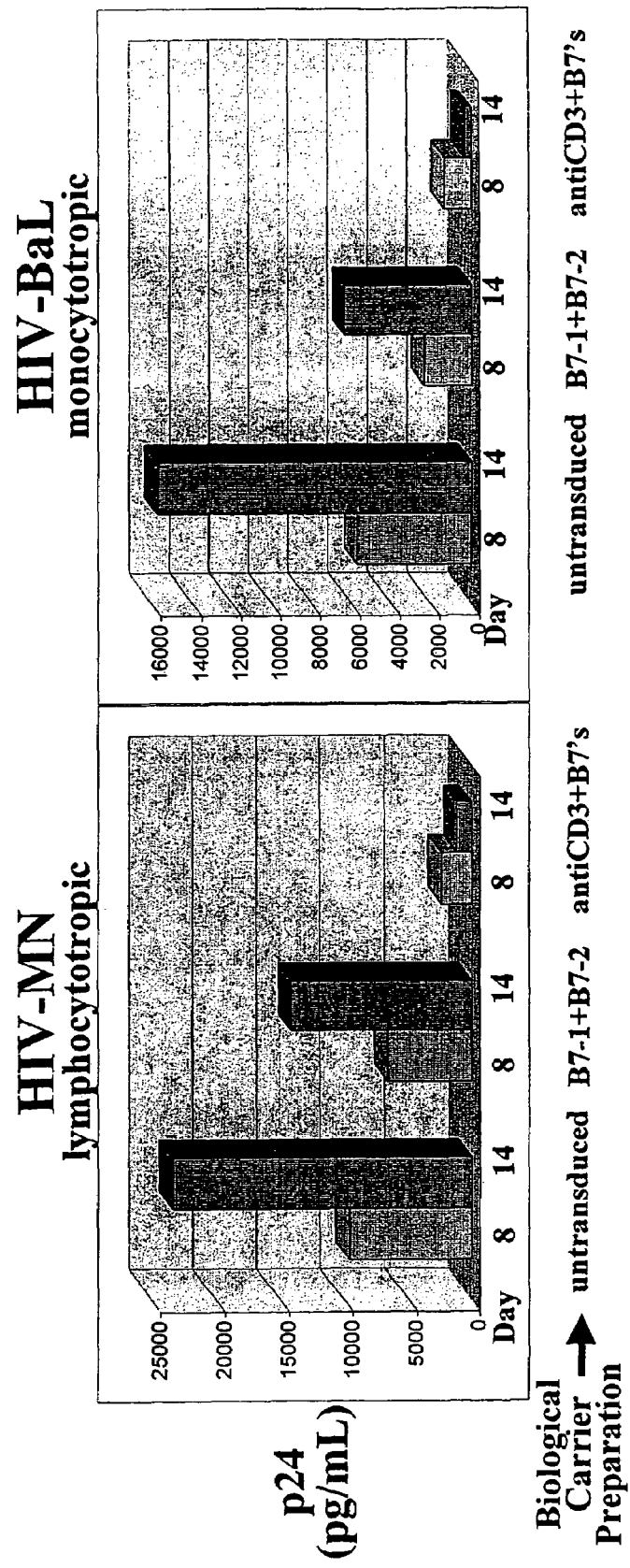
FIG. 9 shows the effects of exposing elutriated T-lymphocytes to HIV-1 based Biological Carrier preparations. Unlike preparations made from untransduced host cells, the Biological Carrier preparations made from host cells modified to express either B7-1+B7-2 or the B7 molecules+an anti CD3 molecule resulted in a dramatic decrease in the ability of HIV-1 (either lymphocytotropic or monocytotropic) to replicate in human peripheral blood T-lymphocytes. This experiment used Donor #9 elutriated lymphocytes.

Inhibition Of HIV-1 Replication Using HIV-1 Based Biological Carrier Preparations The principle of this invention is further demonstrated by experiments using HIV-1 based Biological Carriers to inhibit HIV-1 replication. Four day PHA/IL-2 stimulated elutriated lymphocytes support HIV-1 (both HIV-1 MN and BaL) replication as measured by detection of HIV-1 encoded p24 protein released into the culture supernatant over time (FIG. 8). The addition of HIV-1 based Biological Carrier preparation obtained from untransduced cultures (FIG. 9) showed similar p24 values to the untreated cultures shown in FIG. 8. However, the addition of HIV-1 based Biological Carriers prepared from either the B7-1+B7-2 or the anti-CD3&B7-1+B7-2 transduced cultures inhibited HIV-1 replication (FIG. 9). The degree of inhibition differed in the two preparations; the anti-CD3&B7-1+B7-2 preparation showing the most significant inhibition. The specificity of HIV-1 inhibition to only the HIV-1 based Biological Carriers formed from either B7-1+B7-2 or anti-CD3&B7-1+B7-2 transduced cultures is further demonstrated when HSV-2 based Biological Carrier preparations from either untransduced or anti-CD3&B7-1+B7-2 cultures did not inhibit HIV-1 replication in the same experiment (FIG. 10). The inhibition of HIV-1 replication is not due to the lack of lymphocyte activation. In fact, cultures treated with either the HIV-1 or HSV-2 based Biological Carriers prepared from B7-1+B7-2 transduced cultures show higher stimulation at earlier times (day 4 for HIV and day 6 for HSV-2) than cultures treated with PHA/IL-2 alone (in the absence of Biological Carriers).

EXAMPLE 6

HSV-1 & -2 Specific Antibody Reactivity Induced by Exposure of Peripheral Blood Lymphocytes to HSV-2 Based Biological Carrier Preparations The principle of this invention is further demonstrated by experiments using HSV-2 based Biological Carriers to induce HSV-1 & -2 specific antibody reactivity. Unstimulated peripheral blood elutriated lymphocytes were exposed to either PHA, HSV-2 based or HIV-1 based Biological Barrier preparations (Table 2). After 3, 6, 10 and 14 days in culture, 200 μL aliquot of the cell suspension was placed into four different wells within a 96-well culture plate. Each of the four wells were coated with a lysate from either herpesvirus type-1 (HSV-1), herpesvirus type-2 (HSV-2), human immunodeficiency virus type 1 (HIV-1), or vesicular stomatitis virus (VSV). The cultures were incubated at 37° C. for 3 days, followed by incubation with a hydrogen peroxidase conjugated anti-human IgG antibody and colorimetric substrate for detection of antibodies formed in vitro against the different viruses. The results illustrate the ability of HSV-2 based Biological Carriers, but not HIV-1 based Biological Carriers, to induce HSV-1 & -2 specific reactivity. If neutralizing in nature, this antibody specific response can inhibit HSV-2 reactivation in vivo.

Table 2 shows specific antibody reactivity against HSV-1 & -2 when peripheral blood lymphocytes were exposed to HSV-2 based Biological Carriers (BCs), but not when exposed to HIV-1 based BCs. Donor #9 cells were used in this experiment; donor's plasma was positive for the presence of HSV-1 & -2 antibodies at the time of lymphocyte isolation. The data shows some reactivity at day 10 in PHA-stimulated cultures. In this donor HSV-2 based Biological Carriers prepared from untransduced host cells were HSV-1 & -2 antibody reactive. We would expect that in a HSV-1 & -2 negative donor only Biological Carriers prepared from co-stimulatory molecule transduced host cells would be HSV-1 & -2 antibody reactive positive.

TABLE 2

HSV-1&-2 Specific Antibody Formation Induced by Exposure of Peripheral Blood T-lymphocytes to HSV-2 based Biological Carrier Preparations

| Culture Sample From | Antibody Reactivity Against: | Sample Time Point (relative OD units) Day 3 | Day 6 | Day 10 | Day 14 |
|---|---|---|---|---|---|
| Control | HSV-1 | >4.00 | >4.00 | >4.00 | >4.00 |
| | HSV-2 | 3.09 | 2.993 | >4.00 | 2.688 |
| | HIV-1 | 2.23 | 2.187 | 2.698 | 1.889 |
| | VSV | 0.26 | 0.159 | 0.245 | 0.029 |
| Unstimulated | HSV-1 | 0.007 | 0.012 | ND | 0.001 |
| | HSV-2 | 0.006 | 0.004 | | 0.002 |
| | HIV-1 | 0.003 | 0.007 | | 0.004 |
| | VSV | 0.004 | 0.002 | | 0.004 |
| PHA-stimulated | HSV-1 | 0.005 | 0.036 | 0.586 | 0.060 |
| | HSV-2 | 0.005 | 0.015 | 0.590 | 0.020 |
| | HIV-1 | 0.007 | 0.009 | 0.005 | 0.003 |
| | VSV | 0.004 | 0.002 | 0.005 | 0.002 |
| HSV-2 based BCs | HSV-1 | 0.214 | 1.876 | 3.722 | 0.006 |
| | HSV-2 | 0.163 | 1.744 | 3.503 | 0.003 |
| | HIV-1 | 0.003 | 0.004 | 0.005 | 0.003 |
| | VSV | 0.005 | 0.003 | 0.003 | 0.007 |
| HIV-1 Based BC | HSV-1 | 0.002 | 0.007 | 0.031 | 0.005 |
| | HSV-2 | 0.004 | 0.004 | 0.027 | 0.002 |
| | HIV-1 | 0.004 | 0.001 | 0.005 | 0.001 |
| | VSV | 0.003 | 0.002 | 0.007 | 0.004 |

BC = Biological Carrier;
ND = not done

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A non-infectious biological carrier comprising a Human Immunodeficiency Virus (HIV) viral or viral-like particle that (i) presents at least one exogenous antigen incorporated into said particle such that said at least one antigen initiates an immune response;

(ii) also expresses at least one exogenous antigen fragment bound to a primary host cell surface molecule selected from MHC I and MHC II; and (iii) also expresses at least one B7 molecule as a co-stimulatory molecule.

2. The biological carrier of claim 1 wherein said at least one B7 molecule is selected from B7-1 and B7-2.

3. The biological carrier of claim 1 wherein the exogenous antigen is selected from the group consisting of a protein, a polypeptide, and an antibody.

4. The biological carrier of claim 1 wherein said exogenous antigen is recombinantly produced by a host cell.

5. The biological carrier of claim 4 wherein the exogenous antigen is encoded in an expression vector introduced into the host cell.

6. The biological carrier of claim 4 wherein the exogenous antigen is from a pathogen.

7. The biological carrier of claim 4 wherein the exogenous antigen is from an infectious agent.

8. The biologically constructed particle of claim 4 wherein the exogenous antigen is from a tumor.

9. The biologically constructed particle of claim 8 wherein the tumor antigen is a tumor-specific transplantation antigen.

10. The biologically constructed particle of claim 8 wherein the tumor antigen is a tumor-associated transplantation antigen.

11. The biological carrier of claim 1 wherein said co-stimulatory molecule is recombinantly produced by a host cell.

12. The biological carrier of claim 6 wherein the exogenous antigen is encoded in an expression vector introduced into a host cell.

13. The biological carrier of claim 1 which further contains a cytokine recombinantly produced by a host cell.

14. The biological carrier of claim 1 wherein said particle is derived from acute pathogen infection of a host cell that has been modified to have at least one exogenous recombinant molecule expressed on the host cell surface such that said molecule is incorporated into the particle as the particle is released from the host cell.

15. The biological carrier of claim 14 wherein said particle is derived from a chronically pathogen infected host cell line.

16. A method for inducing an immune response by stimulating presentation of at least one exogenous antigen, said method comprising administering a biological carrier of claim 1 to an animal or human subject.

* * * * *